United States Patent [19]

Duhault

[11] 4,056,623
[45] Nov. 1, 1977

[54] METHODS OF TREATING ANIMALS SUFFERING FROM HYPERLIPIDEMIA USING CERTAIN N-PHENYL SULPHONYL-N'-(3-AZABICYCLOALKYL) UREAS

[75] Inventor: Jacques Duhault, Chatou, France

[73] Assignee: Science Union et Cie, Societe Francaise de Recherche Medicale, Suresnes, France

[21] Appl. No.: 692,387

[22] Filed: June 3, 1976

Related U.S. Application Data

[63] Continuation-in-part of Ser. No. 555,427, March 5, 1975, abandoned.

[51] Int. Cl.² .................... A61K 31/40; A61K 31/445
[52] U.S. Cl. ..................................... 424/274; 424/267
[58] Field of Search ........................ 424/265, 267, 274

[56] References Cited

U.S. PATENT DOCUMENTS 3,501,495  3/1970  Beregi et al. ..................... 424/274 X

OTHER PUBLICATIONS

Merck Manual, 10th Ed., pp. 210–211 (1961).

Primary Examiner—Leonard Schenkman
Attorney, Agent, or Firm—Gordon W. Hueschen

[57] ABSTRACT

Pharmaceutical compositions containing a compound selected from N-phenyl sulphonyl-N'-(3-azabicycloalkyl) ureas or physiologically acceptable salts thereof and an appropriate pharmaceutical carrier for reducing the risk of arteriosclerosis.

5 Claims, No Drawings

METHODS OF TREATING ANIMALS SUFFERING FROM HYPERLIPIDEMIA USING CERTAIN N-PHENYL SULPHONYL-N'-(3-AZABICYCLOALKYL) UREAS

This application is a continuation-in-part of my prior-filed copending application Ser. No. 555,427, filed Mar. 5, 1975 now abandoned. The present invention relates to pharmaceutical compositions and a method for reducing the risk of arteriosclerosis.

More particularly, the invention relates to a method of decreasing the lipid level in the plasma, the liver and the vessels of warm blooded animals and thereby reducing the risk of arteriosclerosis due to lipid infiltration and deposition even when serum cholesterol levels are moderately increased.

The method of the present invention comprises the administration to a warm blooded animal an effective amount of a compound of the formula:

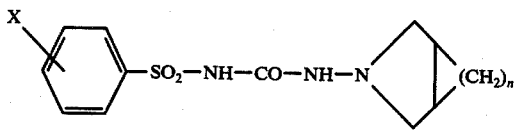

wherein: x is a substituent selected from the group consisting of: halogen, e.g., chloro, bromo, or fluoro, and a lower alkyl radical of 1 to 5 carbon atoms inclusive, e.g., methyl, ethyl, propyl, isopropyl, butyl, secondary butyl, tertiary butyl and amyl, and $n$ is 1 to 3 inclusive, or physiologically tolerable salts thereof.

These N-arylsulphonyl-N'-(3-azabicycloalkyl) areas are known compounds (Cf. U.S. Pat. No. 3,501,495) and can be prepared by reacting an arylsulphonyl urethane with an N-amino-3-azabicycloalkane, according to a process described by Marshall et al. J. Org. Chem. 23. 927 (1958).

Their blood sugar lowering properties are disclosed in the above-cited Patent.

It has now surprisingly been found that the active compounds of the present invention, having the above-identified formula, are able to lower the blood lipid level at dosages as low as 25 mg/kg and prevent lipid infiltration and deposition at dosages which do not decrease the blood sugar level. Such dosages are on the order of 15 mg/kg of body weight. These surprising findings have been demonstrated in rabbits fed a diet containing 0.5 percent cholesterol for a total period of 35 days. Blood lipid levels are found to be reduced at dosages as low as 25 mg/kg and lipid infiltration and deposition in X-ray damaged carotid arteries were prevented at 15 mg/kg of body weight, at which latter dosages the blood sugar level was not decreased. By the prevention of infiltration and deposition of lipids, atheroma, which may be condsidered as the first step of arteriosclerosis, is also prevented, as will be recognized by one skilled in the art.

It is known that one of the most important risk factors for arteriosclerosis is an increased blood level of lipids, i.e., cholesterol and triglycerides. It was completely in concordance with this knowledge the finding of a significant decrease of arteriosclerosis in the blood vessels of the treated animals when compared with those of untreated.

The above findings permit the treatment of warm blooded animals afflicted with hyperlipidemia by the compounds of the present invention thus reducing the risk of arteriosclerosis. The compounds may be administered, together with appropriate pharmaceutical carriers, in various pharmaceutical forms for oral, rectal or parenteral administration. As carriers, there may be mentioned for example, starch, talc, lactose, magnesium stearate, ethyl cellulose, distilled water or cocoabutter. The doses may be ranged from 10 to 100 mg, 1/5 times in a day.

The following example illustrates a pharmaceutical composition of the present invention.

| Example: | |
|---|---|
| N-(4-methylbenzenesulphonyl)-N'-[3-azabicyclo(3,3,0)-3-octyl] urea | 0.060 g |
| Lactose | 0.050 g |
| Arabic gum | 0.015 g |
| Stearate of Magnesium | 0.003 g |
| Talc | 0.008 g |
| for a tablet or dragee of: | 0.136 g |

I claim:

1. A method of treating a warm-blooded animal suffering from hyperlipidemia to effect improvement in such condition and thereby reduce the risk of arteriosclerosis, which consists of administering to such animal an effective anti-lipid infiltration and deposition amount of a compound selected from the group consisting of:

A. an N-benzenesulphonyl-N'-(3-azabicycloalkyl) urea of the formula:

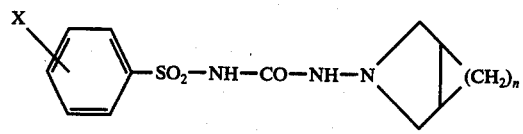

wherein: X is a substituent selected from the group consisting of chloro, bromo, fluoro, and a lower-alkyl radical of 1 to 5 carbon atoms, inclusive; and $n$ is 1 to 3, inclusive; and B. a physiologically tolerable addition salt thereof.

2. The method according to claim 1, wherein $n$ is 3.

3. The method according to claim 2, wherein X is lower-alkyl.

4. The method according to claim 3, wherein the lower-alkly group is methyl and the compound is N-(4-methylbenzenesulphonyl)-N'-[3-azabicyclo(3,3,0)-3-octyl] urea.

5. The method according to claim 4 wherein the compound is administered at a dosage rate of up to about 15 mg/kg of body weight.